(12) United States Patent
Kwon et al.

(10) Patent No.: US 6,929,473 B2
(45) Date of Patent: Aug. 16, 2005

(54) READY-MADE CUSTOMIZED IMPRESSION TRAY FOR FABRICATING AND FITTING DENTURES

(76) Inventors: Chil-Soo Kwon, 103-1506, Bando Bora APT, Gaegum 3-Dong, Busanjin-Gu, Busan (KR); Ki-Bum Kwon, 103-1506, Bando Bora APT, Gaegum 3-Dong, Busanjin-Gu, Busan (KR)

( * ) Notice: Subject to any disclaimer, the term of this patent is extended or adjusted under 35 U.S.C. 154(b) by 45 days.

(21) Appl. No.: 10/414,977

(22) Filed: Apr. 16, 2003

(65) Prior Publication Data

US 2003/0180681 A1 Sep. 25, 2003

Related U.S. Application Data

(63) Continuation of application No. PCT/KR01/01731, filed on Oct. 15, 2001.

(30) Foreign Application Priority Data

Oct. 19, 2000 (KR) .................................... 2000/0061543

(51) Int. Cl.$^7$ ................................................ A61C 9/00
(52) U.S. Cl. ............................ 433/37; 433/45; 433/214
(58) Field of Search ............................. 433/37, 41, 43, 433/45, 214, 38, 44, 47

(56) References Cited

U.S. PATENT DOCUMENTS

| | | | | |
|---|---|---|---|---|
| 3,978,585 A | * | 9/1976 | Holcomb | 433/41 |
| 4,368,040 A | * | 1/1983 | Weissman | 433/36 |
| 4,375,965 A | * | 3/1983 | Weissman | 433/37 |
| 5,340,308 A | * | 8/1994 | Cukjati | 433/41 |
| 5,551,872 A | * | 9/1996 | Mena | 433/37 |
| 6,227,852 B1 | * | 5/2001 | Schedler et al. | 433/37 |
| 6,302,690 B1 | * | 10/2001 | Brandhorst et al. | 433/45 |

* cited by examiner

Primary Examiner—Cary E. O'Connor
(74) Attorney, Agent, or Firm—St. Onge Steward Johnston & Reens LLC

(57) ABSTRACT

The present invention relates to a ready-made customized impression tray for fabricating and fitting dentures more specifically, a method and apparatus for producing denture using the tray and changing the structure of the tray required for producing the denture to simultaneously measure the shape and height of the denture which is implanted to be fitted to the upper and lower jaws so that the producing processes of the denture can make simple.

According to the invention, it provides a method and apparatus for producing denture using the tray capable of producing denture suitable for an oral structure of a patient in fast and simply manner by forming a shape measuring tray for a partial denture which forms a through hole portion exposing an alveolar into the upper of tray measuring the shape of alveolar into which missing teeth and normal teeth are arranged and the height of denture to be implanted into it to adhere a plural number of caps for normal teeth and plate for missing teeth to the through hole portion, and forming the plate for missing teeth for adhering paraffin measuring the height of denture to the its upper, respectively, to simultaneously check the shape of alveolar and a proper height of denture.

4 Claims, 4 Drawing Sheets

READY-MADE CUSTOMIZED IMPRESSION TRAY FOR FABRICATING AND FITTING DENTURES

This application is a continuation of pending International Patent Application No. PCT/KR01/01731 filed Oct. 15, 2001, which designates the United States and claims priority of pending Korean Application No. 2000/0061543 filed Oct. 19, 2000.

TECHNICAL FIELD OF THE INVENTION

The present invention relates to a ready-made customized impression tray for fabricating dentures more specifically, to a method and apparatus for producing denture using the impression tray of a particular construction to conveniently measure the shape and height of the denture to be implanted in the upper and lower jaws so that the producing processes of the denture can be made more simple.

BACKGROUND OF THE INVENTION

Typically, in order to implant denture into missing teeth, the shape and height of teeth for each person is measured during dental surgery and then the denture is produced in the dental laboratory according to the measured shape to fit into the oral structure of each person.

In a conventional art, when producing denture, a mold is made into which normal teeth and missing teeth of a patient are impressed with a wax rim in a sol or resilient state which is not harmful to human beings, the wax rim being adhered into the tray selected to be suitable for the shape of teeth according to alveolar and measures with paraffin the height of denture which is intended to implant the paraffin causing the denture produced to be fitted to an oral structure according to the mold to attach to the missing teeth of frame.

This conventional method divides the measurement and production into a dental surgery and the production of the denture in a dental laboratory, respectively, i.e. this method measures the shape of alveolar in dental surgery, produces the frame to be fitted to the shape of alveolar, again measuring the height of denture which is intended to be implanted during the dental surgery, and producing the denture in the dental laboratory.

This kind of method inconveniences a patient by separately proceeding with the measurement for the shape of alveolar and the height of denture, and by repetitively measuring and producing the shape of alveolar and the height of denture in dental surgery and in the dental laboratory, respectively.

Furthermore, it increases the medical treatment cost by requiring additional dental laboratory work because it is difficult to ascertain the accurate height of normal teeth in a cutting portion of teeth when remedying damaged teeth by carious teeth, etc.

In order to improve the time consuming and cumbersome procedures, there was need for a method and apparatus that could eliminate many steps and reduce the amount of time required.

For examples, U.S. Pat. No. 5,961,325 teaches that a dentist can directly take impressions of the patient's upper and lower arches using bite block/impression tray and a preset teeth carrying tray, and U.S. Pat. No. 5,520,539 shows a two-part impression tray consisting of a basic impression tray and of a paired impression tray freely arrangeable and positioned in order to improve the complicated procedures for producing denture. But these kinds of methods and apparatus are still lacking in solving the problems of significant time or unnecessary process for producing denture of the prior structure of the trays not being built based upon practical considerations and effectiveness.

SUMMARY OF THE INVENTION

The object of the present invention overcomes the problems described above and provides a new ready-made tray. It provides a method and apparatus for producing a denture using a tray, namely, the ready-made customized impression tray which is capable of producing a denture suitable for an oral structure of a patient in fast and simple manner. The invention provides a shape measuring tray (A) for a partial denture which has a through hole portion for exposing an alveolar into the upper of tray and measuring the shape of alveolar along which missing teeth and normal teeth are arranged. The invention further provides a height measuring tray (B) for a partial denture for measuring or determining the height of denture to be implanted. The trays include a plural number of caps for normal teeth and plates for missing teeth attached the frame of the trays and paraffin for measuring the height of denture for simultaneously checking the shape of alveolar and a proper height of denture.

DETAILED DESCRIPTION OF PREFERRED EMBODIMENTS

Figure 1:
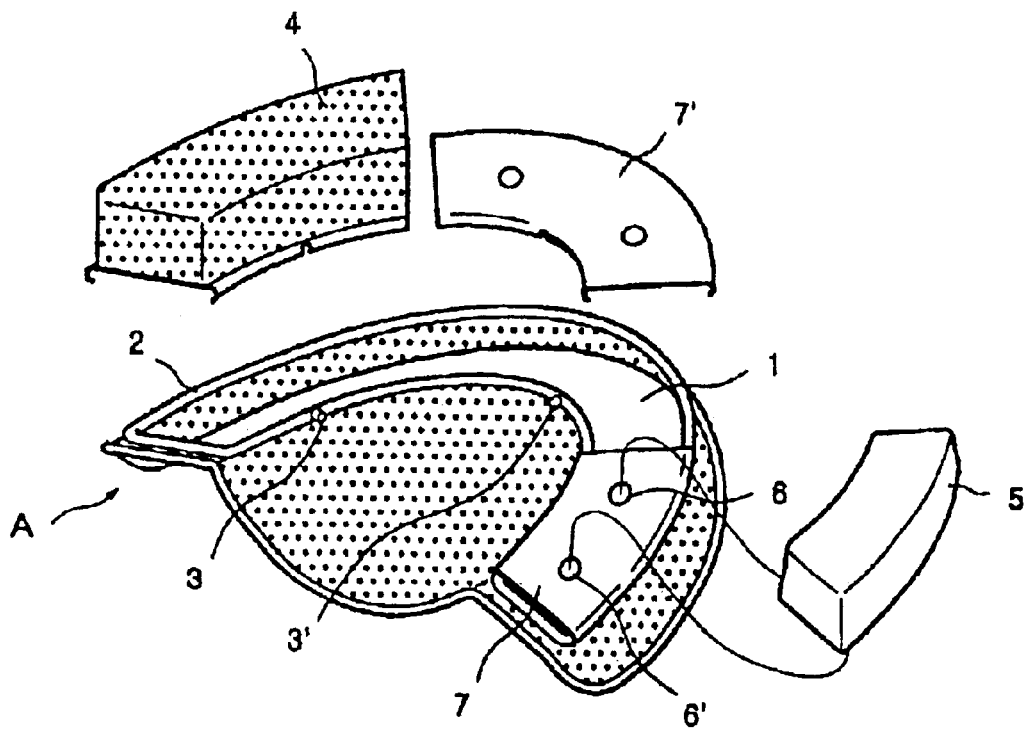
FIG. 1 shows one exemplary embodiment of the invention illustrating a cap and a plate with a tray for a partial denture of the invention.

The present invention will now be described with reference to the accompanying drawings.

The present invention provides a frame for denture including a tray having an oral or jaw-like shape and a mold for impression of denture. The inventive apparatus for producing a denture provides, for producing a partial denture, a shape measuring tray (A) and a height measuring tray (B) for, respectively, measuring the shape of alveolar into which missing teeth and normal teeth are arranged and the height of denture to be implanted. Each of the trays (A) and (B) include a fixture frame (2) having an inner through hole portion (1) for contact with the alveolar, and a plural number of protrusions (3,3') formed along the outer peripheral portion of the fixture frame (2). In the shape measuring tray (A), fixes a plural number of caps for normal teeth (4) for checking or copying the shape of alveolar into which the normal teeth and the missing teeth are arranged and plates (7,7') for missing teeth into which inserting holes(6, 6') are penetrated and having paraffin (5) attached to the fixture frame (2) utilizing the protrusions (3,3') of the fixture frame (2) in the height measuring tray (B), attaches the plates (7,7') for missing teeth with the paraffin (5) for checking or determining the height of denture attached to the upper side of the fixture frame (2) and the protrusions (3,3') of the fixture frame(2).

Figure 3:
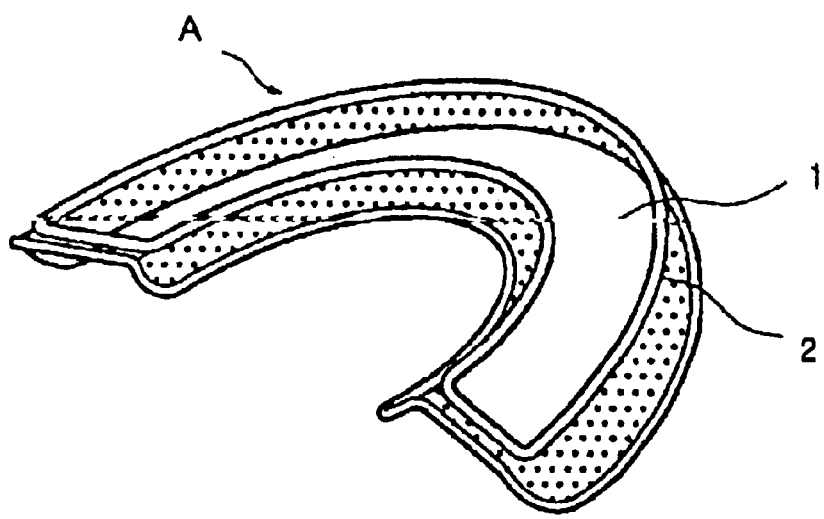
FIG. 3 shows an example of a tray for a partial denture of the invention.
Figure 4:
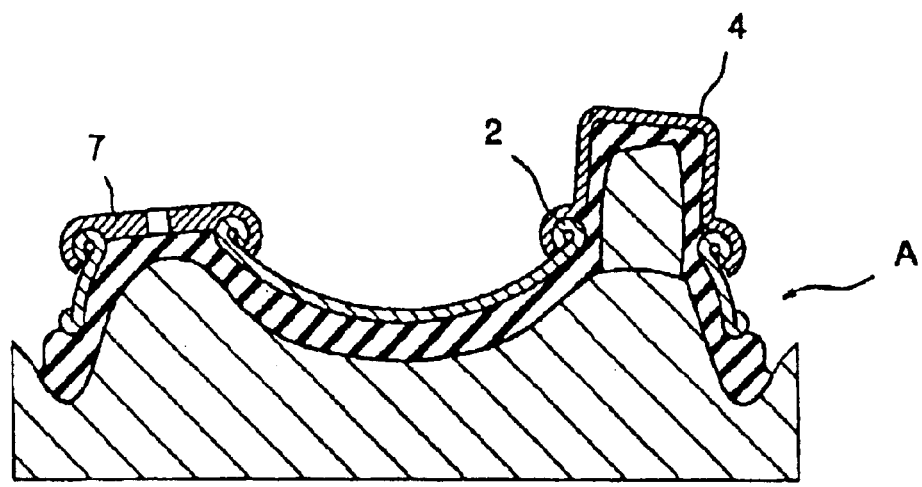
FIG. 4 is a sectional view illustrating a shape measuring tray of the invention utilized to develop or copy the shape of alveolar according to the principles of the invention.
Figure 5:
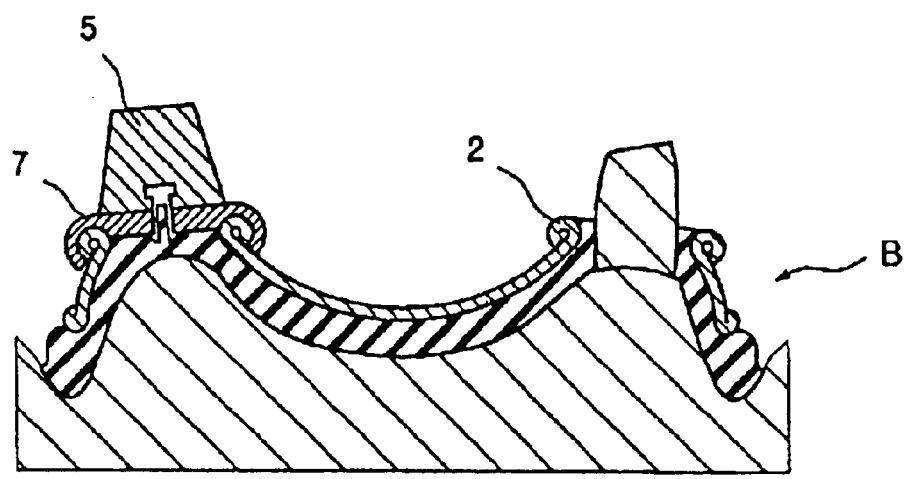
FIG. 5 and FIG. 6 are respectively a sectional view illustrating a height measuring tray of the invention for measuring the height of denture according to the principles of the invention.
Figure 6:
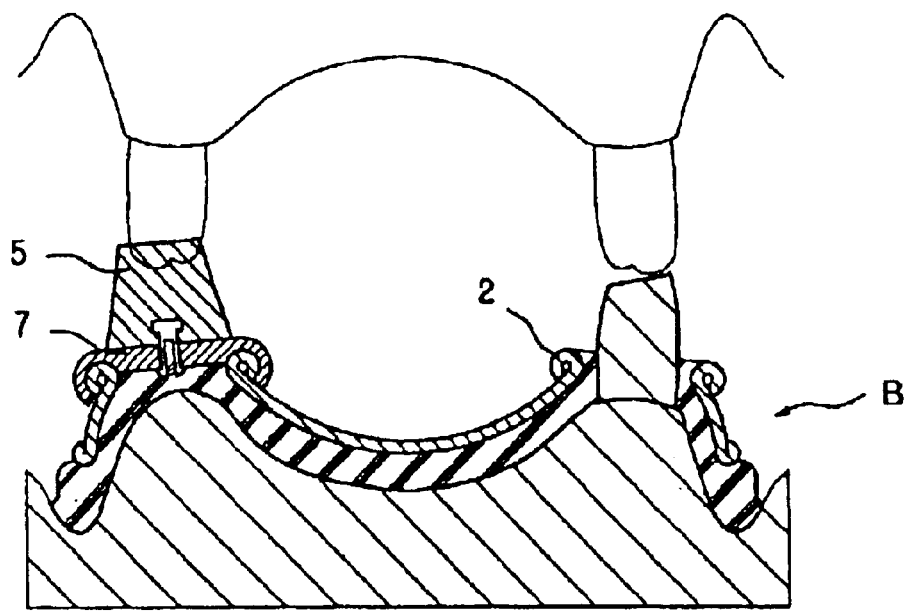

Furthermore, the invention provides a method of producing denture suitable for oral structure by measuring or copying the shape of alveolar into which teeth are arranged with a tray having a wax rim attached to the inner side of the tray generally having the shape of oral, and by determining the height of denture with a frame for denture on which the paraffin (5) is attached. The inventive method for producing denture using a tray further includes a fabricating step (100) for producing a pair of trays for partial denture (A, B) having a through hole portion (1) for exposing alveolar into which missing teeth and normal teeth are arranged and a tray for full denture (C) having inserting holes (6,6') for attaching paraffin (5') with the overall shape of alveolar in the upper contact portion of alveolar in which the full teeth are missing, i.e. not having any normal teeth as shown in FIG. 1 or FIG. 3. The inventive method further includes a step (200) for forming the shape of alveolar by impression after adhering a plural number of caps (4) and plates (7,7') to the through hole portion (1) of the shape measuring tray (A), as shown in FIG. 4, and a step (300) for measuring the height of denture intended to implant by attaching the paraffin(5) to the upper surface of the plates(7,7') adhered to the height measuring tray for partial denture(B) and measuring the height of the missing teeth upon impression, as shown in FIG. 5 and FIG. 6, and producing (400) denture through the steps.

The invention forms a shape measuring tray (A) for partial denture for impressing the shape of alveolar into which normal teeth and missing teeth are arranged and a height measuring tray (B) for partial denture for checking or determining the proper height of denture intended to be implanted, and a tray for full denture (C) impressing the shape of alveolar in which the full teeth are missing, i.e. not having any normal teeth, respectively, to produce a denture having the shape of alveolar and the proper height suitable for an oral structure of a patient in fast and simple manner according to the patient's regular set of teeth. The operation of the invention will now be described below.

Figure 2:
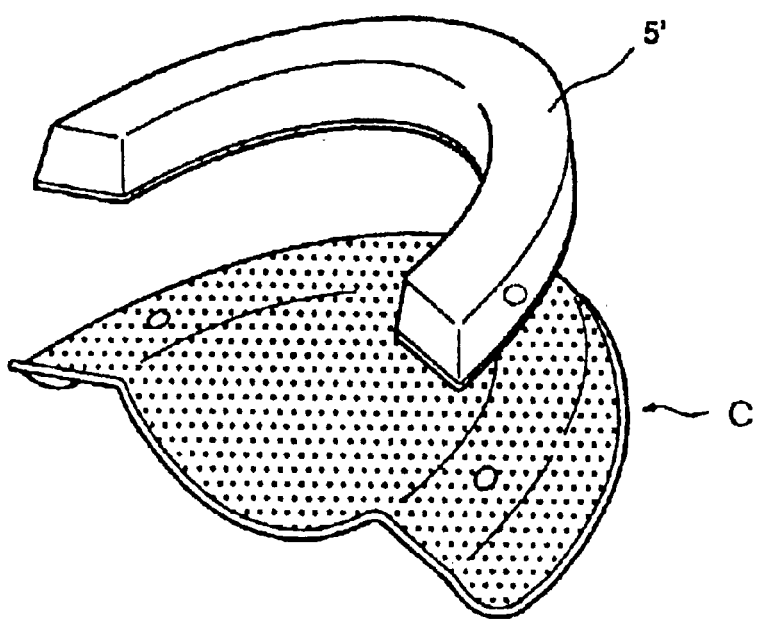
FIG. 2 shows paraffin for attaching with a tray for a full denture of the invention.

First, as shown in FIG. 1, the alveolar into which normal teeth and missing teeth are arranged is exposed to the shape measuring tray (A) for partial denture and the upper surface of the through hole portion (1) to impress the accurate shape of alveolar fitted to the oral structure of patient by fixing the plural number of caps (4) impressing the shape of alveolar into which normal teeth and missing teeth are arranged and the plates (7,7') for missing teeth into the fixture frame (2) and the protrusions (3, 3') formed along the outer peripheral of the through hole portion(1), and as shown in FIG. 2 and FIG. 3, the paraffin (5) is attached to the inserting holes (6, 6') of the plates (7, 7') for missing teeth which are adhered to the upper surface of the height measuring tray (B) for a partial denture so that it coincides with the height of normal teeth exposed to the through hole portion (1), thereby mixing the normal teeth in which the upper jaw and the lower jaw are exposed to the through hole portion(1) with the paraffin to accurately impress the height of denture intended to be implanted.

Figure 7:
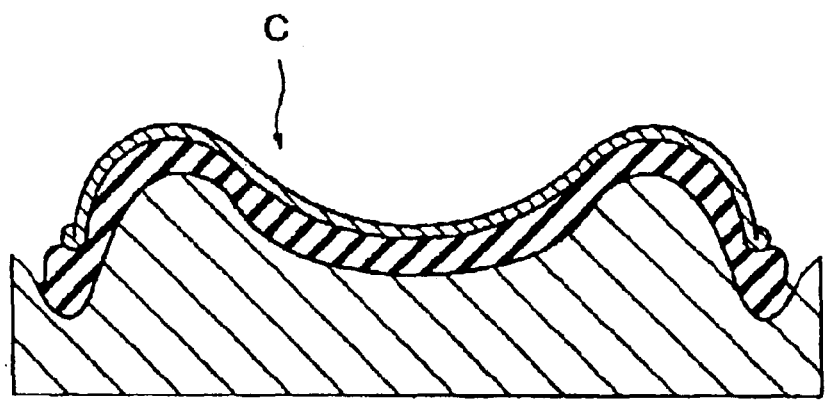
FIG. 7 is a sectional view illustrating a tray for a total denture according to the invention.
Figure 8:
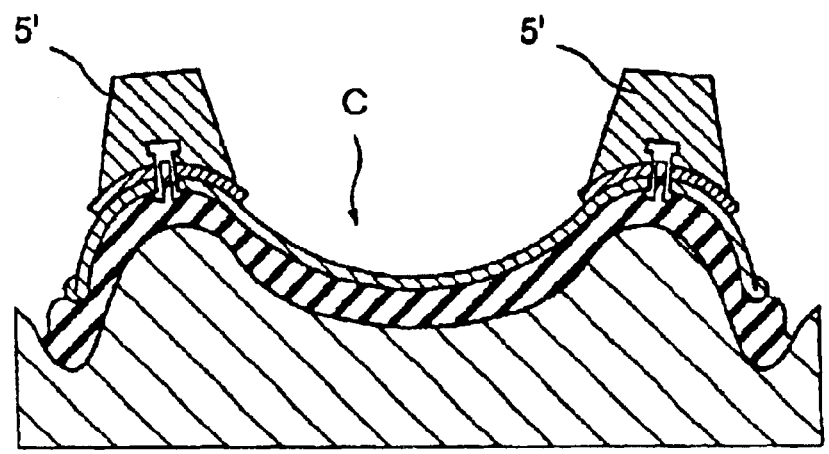
FIG. 8 is a sectional view illustrating the state to which paraffin in the shape of alveolar in FIG. 7 is attached.

Also, the operation for missing teeth of full teeth not having normal teeth is omitted since it performs the same operation as that described above by attaching the paraffin (5') in the shape of alveolar to the inserting holes (6,6') penetrated into the tray (C) for full teeth as shown FIG. 7 and FIG. 8.

Industrial Applicability

The invention forms a shape measuring tray (A) for a partial denture impressing the shape of alveolar and a height measuring tray (B) for partial denture checking the height of denture, and a tray for full teeth (C) not having normal teeth, respectively, and selectively attaches a cap (4) for normal teeth and plates (7,7') for missing teeth or a paraffin (5') in the shape of alveolar, according to a regular set of teeth of the patient, thereby simultaneously impressing and checking the shape of alveolar and the height of denture to reduce the number of trips between the dental surgery and the dental laboratory, and the number of visits by the patient for producing denture, as well as saving the medical treatment cost by reducing the production period and also to improving convenience in use by fitting the damaged teeth to normal teeth through a through hole (1) of a tray to easily remedy the damaged teeth as well as to apply in various uses, such as the production of denture and the remedy of the damaged teeth, etc.

What is claimed is:

1. An apparatus for fabricating dentures comprising;
    a shape measuring tray for partial denture for measuring or copying the shape of alveolar having missing teeth and normal teeth arranged therein
    a height measuring tray for partial denture for measuring the height of denture to be implanted, each of the shape measuring tray and the height measuring tray including a fixture frame with a through hole defined in the fixture frame and a plurality of engagement elements formed along the fixture frame;
    a plurality of caps having a generally U-like inner surface configured to receive a wax rim therein for copying the shape of alveolar along which the normal teeth and the missing teeth being arranged; and
    at least one plate attached on the fixture frame of the height measuring tray, the at least one plate adapted to attach paraffin thereon for measuring the height of denture to be implanted.

2. The apparatus according to claim 1, further comprising a tray for full denture, the tray for full denture including a fixture frame with a through hole defined in the fixture frame and a plurality of engagement elements formed along the fixture frame for attaching paraffin thereto for fabrication of the full denture.

3. A method for producing denture by measuring the shape of alveolar along which teeth are arranged with an impression tray having a wax rim attached to the inner side of the tray and by measuring the height of denture with paraffin attached on the tray, the method for producing denture comprising the steps of:
    a) producing a shape measuring tray for partial denture and a height measuring tray for partial denture, each of the trays having a through hole thereon for exposing alveolar along which missing teeth and normal teeth are arranged, the height measuring tray having paraffin attached thereon for measuring the height of denture intended to implant;
    b) forming the shape of alveolar by impression with the shape measuring tray for partial denture, the shape measuring tray having a plural number of caps with a wax rim attached to the inner side of the caps;
    c) measuring the height of denture intended to implant upon impression with the paraffin of the height measuring tray for partial denture; and
    d) producing denture using the shape measuring tray with the shape of alveolar formed therein and the height measuring tray with the height of denture intended to implant impressed in the paraffin.

4. The method for producing denture according to claim 3, further comprising the steps of producing a tray for full denture having paraffin attached thereon and measuring the height of full denture by impression with the tray for full denture.

* * * * *